US010094826B2

(12) United States Patent
Andres et al.

(10) Patent No.: US 10,094,826 B2
(45) Date of Patent: Oct. 9, 2018

(54) METHOD OF ASSESSING RHEUMATOID ARTHRITIS BY MEASURING ANTI-CCP AND ANTI-PIK3CD

(71) Applicant: Roche Diagnostics Operations, Inc., Indianapolis, IN (US)

(72) Inventors: Herbert Andres, Penzberg (DE); Stefan Weiser, Seehausen (DE); Johann Karl, Peissenberg (DE); Ursula Kunert, Munich (DE); Florian Grupp, Iffeldorf (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 15/673,976

(22) Filed: Aug. 10, 2017

(65) Prior Publication Data

US 2018/0003710 A1 Jan. 4, 2018

Related U.S. Application Data

(63) Continuation of application No. PCT/EP2016/052610, filed on Feb. 8, 2016.

(30) Foreign Application Priority Data

Feb. 13, 2015 (EP) .................... 15155064

(51) Int. Cl.
| | | |
|---|---|---|
| *G01N 33/53* | (2006.01) | |
| *G01N 33/564* | (2006.01) | |
| *G01N 33/563* | (2006.01) | |
| *G01N 33/58* | (2006.01) | |

(52) U.S. Cl.
CPC ......... *G01N 33/564* (2013.01); *G01N 33/563* (2013.01); *G01N 33/58* (2013.01); *G01N 2333/91215* (2013.01); *G01N 2800/102* (2013.01)

(58) Field of Classification Search
None
See application file for complete search history.

(56) References Cited

U.S. PATENT DOCUMENTS

| | | | | |
|---|---|---|---|---|
| 4,444,879 A | * | 4/1984 | Foster .................. | G01N 33/545 422/400 |
| 5,807,522 A | | 9/1998 | Brown et al. | |

FOREIGN PATENT DOCUMENTS

| | | |
|---|---|---|
| WO | 1998/008946 A1 | 3/1998 |
| WO | 1998/022503 A2 | 5/1998 |
| WO | 1999/028344 A2 | 6/1999 |
| WO | 1999/035167 A1 | 7/1999 |
| WO | 2001/046222 A2 | 6/2001 |
| WO | 2003/050542 A2 | 6/2003 |
| WO | 2005/064307 A2 | 7/2005 |
| WO | 2005/085858 A1 | 9/2005 |
| WO | 2007/039280 A1 | 4/2007 |
| WO | 2008/064336 A2 | 5/2008 |
| WO | 2009/036768 A2 | 3/2009 |

OTHER PUBLICATIONS

Van Der Vekiens et al., Human and equine cardiovascular endocrinology: beware to compare, Cardiovascular Endocrinology 2013, vol. 2, No. 4, pp. 67-76. (Year: 2013).*
Torzewski et al., Animal Models of C-Reactive Protein, Hindawl Publishing Corporation, Mediators of Inflammation, vol. 2014, Article ID 683598, 2014, pp. 1-7. (Year: 2014).*
Arnett, Frank C. et al., The American Rheumatism Association 1987 Revised Criteria for the Classification of Rheumatoid Arthritis, Arthritis and Rheumatism, 1988, pp. 315-324, vol. 31, No. 3.
Ballara, Sundeept et al., Raised Serum Vascular Endothelial Growth Factor Levels Are Associated With Destructive Change in Inflammatory Arthritis, Arthritis & Rheumatism, 2001, pp. 2055-2064, vol. 44, No. 9.
Bax, Marieke et al., The pathogenic potential of autoreactive antibodies in rheumatoid arthritis, Seminars in Immunopathology, 2014, pp. 313-325, vol. 36.
Breiman, Leo, Random Forests, Machine Learning, 2001, pp. 5-32, vol. 45.
Brenchley, P. E. C., Angiogenesis in inflammatory joint disease: a target for therapeutic intervention, Clinical & Experimental Immunology, 2000, pp. 462-429, vol. 121.
Friedman, Jerome H., Regularized Discriminant Analysis, Journal of the American Statistical Association, 1989, pp. 165-175, vol. 84, No. 405.
Hornauer, Hans et al., IMPACT—a protein array technology for the diagnostic application of the future, BIOspectrum, 2004, pp. 564-565, vol. 10.

(Continued)

*Primary Examiner* — Gary Counts
(74) *Attorney, Agent, or Firm* — Roche Diagnostics Operations, Inc.

(57) ABSTRACT

Described is a method aiding in the assessment of rheumatoid arthritis ("RA"). The method is used in assessing RA in vitro. It is practiced by analyzing biochemical markers, including measuring the concentration of anti-CCP and anti-PIK 3CD and correlating the concentrations determined to the absence or presence of RA. Also disclosed is the use of a marker panel including anti-CCP and anti-PIK3CD in the diagnosis of RA and it teaches a kit for performing the method. Also described is the use of a marker panel comprising anti-CCP and anti-PIK3CD to differentiate RA from other autoimmune diseases, preferably osteoarthritis (OA).

8 Claims, No Drawings

Specification includes a Sequence Listing.

(56) References Cited

OTHER PUBLICATIONS

Hornauer, Hans et al., Protein array technology for the diagnostic application of the future: IMPACT, Laborwelt, 2004, pp. 38-39, vol. 4.

International Search Report dated Mar. 22, 2016, in Application No. PCT/EP2016/052610, 5 pages.

Kellgren, J. H. and Lawrence, J. S. Radiological Assessment of Osteo-Arthrosis, Annals of the Rheumatic Diseases, 1957, pp. 494-502, vol. 16.

Lee, S.-S. et al., Vascular endothelial growth factor levels in the serum and synovial fluid of patients with rheumatoid arthritis, Clinical and Experimental Rheumatology, 2001, pp. 321-324, vol. 19.

Robinson, William H. et al., Autoantigen microarrays for multiplex characterization of autoantibody responses, Nature Medicine, 2002, pp. 295-301, vol. 8, No. 3.

Robinson, William H. et al., Proteomics Technologies for the Study of Autoimmune Disease, Arthritis & Rheumatism, 2002, pp. 885-893, vol. 46, No. 4.

Ruczinski, Ingo et al., Logic Regression, Journal of Computational and Graphical Statistics, 2003, pp. 475-511, vol. 12, No. 3.

Schellekens, Gerard A. et al., The Diagnostic Properties of Rheumatoid Arthritis Antibodies Recognizing a Cyclic Citrullinated Peptide, Arthritis and Rheumatism, 2000, pp. 155-163, vol. 43, No. 1.

Tijssen, P., Preparation of enzyme-antibody or other enzyme-macromolecule conjugates, Practice and Theory of Enzyme Immunoassays, 1990, pp. 221-278, Ch. 11, Elsevier, Amsterdam.

Van Der Heijde, D. M. F. M., Joint Erosions and Patients with Early Rheumatoid Arthritis, British Journal of Rheumatology, 1995, pp. 74-78, vol. 34, Supplement 2.

Zweig, Mark H. and Campbell, Gregory, Receiver-Operating Characteristic (ROC) Plots: A Fundamental Evaluation Tool in Clinical Medicine, Clinical Chemistry, 1993, pp. 561-577, vol. 39, No. 4.

Gout, Ivan et al., Expression and characterization of the p85 subunit of the phosphatidylinositol 3-kinase complex and a related p85β protein by using the baculovirus expression system, Biochemistry Journal, 1992, pp. 395-405, vol. 288.

Gómara, M. J. et al., Citrullinated peptides in the diagnosis of rheumatoid arthritis, Current Topics in Medicinal Chemistry, 2013, pp. 743-751, Abstract only, vol. 13, No. 6.

* cited by examiner

METHOD OF ASSESSING RHEUMATOID ARTHRITIS BY MEASURING ANTI-CCP AND ANTI-PIK3CD

CROSS-REFERENCE TO RELATED APPLICATIONS

This application is a continuation of International Application No. PCT/EP2016/052610 filed Feb. 8, 2016, which claims priority to European Application No. 15155064.7 filed Feb. 13, 2015, the disclosures of which are hereby incorporated by reference in their entirety.

SUMMARY

The present invention relates to a method aiding in the assessment of rheumatoid arthritis ("RA"). The method especially is used in assessing the absence or presence of rheumatoid arthritis in vitro. The method is for example practiced by analyzing biochemical markers, comprising measuring in a sample the concentration of anti-CCP and anti-PIK3CD and correlating the concentrations determined to the absence or presence of rheumatoid arthritis. To further improve the assessment of RA in a method of this invention the level of one or more additional marker may be determined together with anti-CCP and anti-PIK3CD and be correlated to the absence or presence of RA. The invention also relates to the use of a marker panel comprising anti-CCP and anti-PIK3CD in the diagnosis of rheumatoid arthritis and it teaches a kit for performing the method of the invention. Further the invention relates to the use of a marker panel comprising anti-CCP and anti-PIK3CD to differentiate RA from other autoimmune diseases, preferably osteoarthritis (OA).

Rheumatoid arthritis ("RA") is a chronic, inflammatory, systemic disease that produces its most prominent manifestations in affected joints, particularly those of the hands and feet. The onset of rheumatoid arthritis can occur slowly, ranging from a few weeks to a few months, or the condition can surface rapidly in an acute manner.

RA has a worldwide distribution and involves all ethnic groups. Although the disease can occur at any age, the prevalence increases with age and the peak incidence is between the fourth and sixth decade. The prevalence estimates for the North American population vary from 0.3% to 1.5%. Today, over 2,500,000 individuals are diagnosed with rheumatoid arthritis in the United States alone, with some statistics indicating from 6.5 to 8 million potentially afflicted with the disease. Women are affected 2-3 times more often than men.

The early symptoms of rheumatoid arthritis are mostly joint specific such as painful joints with joint swelling or tenderness, but may also include rather non-specific manifestations like stiffness, fever, subcutaneous nodules, and fatigue. Very characteristic is the symmetric involvement of joints. The joints of the hands, feet, knees and wrists are most commonly affected, with eventual involvement of the hips, elbows and shoulders. As the disease progresses, any type of motion becomes very painful and difficult leading eventually to a loss of function of the involved joints The more severe cases of rheumatoid arthritis can lead to intense pain and joint destruction. Some 300,000 bone and joint replacement surgical procedures are performed annually in an effort to alleviate the pain and mobility loss resultant from arthritis related joint destruction.

The most widely used system to classify RA used to be the American College of Rheumatology 1987 revised criteria for the classification of RA. (Arnett, F. C., et al., Arthritis Rheum. 31 (1988) 315-324). In 2010 the ACR/EULAR replaced this practice by defining a new approach explained by the following list (taken from Mjaavatten and Bykerk, Best Practice & Research Clinical Rheumatology, 2010):

The ACR/EULAR 2010 classification criteria for RA. A score of 6 or more classifies a patient as definite RA.

| | Points |
|---|---|
| JOINTS (0-5) | |
| 1 large joint | 0 |
| 2-10 large joints | 1 |
| 1-3 small joints (large joints not counted) | 2 |
| 4-10 small joints (large joints not counted) | 3 |
| >10 joints (at least one small joint) | 5 |
| SEROLOGY (0-3) | |
| Negative RF AND negative ACPA | 0 |
| Low positive RF OR low positive ACPA | 2 |
| High positive OR high positive ACPA | 3 |
| SYMPTOM DURATION (0-1) | |
| <6 weeks | 0 |
| ≥6 weeks | 1 |
| ACUTE PHASE REACTANTS (0-1) | |
| Normal CRP AND ESR | 0 |
| Abnormal CRP OR ESR | 1 |

Patients should have at least 1 joint with definite clinical synovitis (swelling), with the synovitis not better explained by another disease. ACR, American College of Rheumatology; EULAR, European League Against Rheumatism; RF, rheumatoid factor; ACPA, anti-citrullinated protein antibody; CRP, C-reactive protein; ESR, erythrocyte sedimentation rate.

The only biochemical markers generally accepted (see the above criteria) and aiding in the diagnosis of RA are the rheumatoid factor (RF), anti-CCP (termed ACPA above) and CRP as detected in serum.

The histological changes in RA are not disease-specific but largely depend on the organ involved. The primary inflammatory joint lesion involves the synovium. The earliest changes are injury to the synovial microvasculature with occlusion of the lumen, swelling of endothelial cells, and gaps between endothelial cells, as documented by electron microscopy. This stage is usually associated with mild proliferation of the superficial lining cell layer. Two cell types constitute the synovial lining: bone marrow derived type A synoviocyte, which has macrophage features, and mesenchymal type B synoviocyte. Both cell types contribute to synovial hyperplasia, suggesting a paracrine interaction between these two cell types. This stage of inflammation is associated with congestion, oedema, and fibrin exudation. Cellular infiltration occurs in early disease and initially consists mainly of T lymphocytes. As a consequence of inflammation, the synovium becomes hypertrophic from the proliferation of blood vessels and synovial fibroblasts and from multiplication and enlargement of the synovial lining layers.

Granulation tissue extends to the cartilage and is known as pannus. The tissue actively invades and destroys the periarticular bone and cartilage at the margin between synovium and bone, known as erosive RA.

The articular manifestations of RA can be placed in two categories: reversible signs and symptoms related to inflammatory synovitis and irreversible structural damage caused by synovitis. This concept is useful not only for staging disease and determining prognosis but also for selecting medical or surgical treatment. Structural damage in the typical patient usually begins sometime between the first and second year of the disease (Van der Heijde, D. M., Br. J. Rheumatol. 34 (1995) 74-78). Although synovitis tends to follow a fluctuating pattern, structural damage progresses as a linear function of the amount of prior synovitis.

The aetiology of the early events in RA remains elusive. An autoimmune component is widely accepted today but other factors are still disputed. The possibility of a bacterial or viral infection has been vigorously pursued. All efforts to associate an infectious agent with RA by isolation, electron microscopy, or molecular biology have failed. It is possible that there is no single primary cause of RA and that different mechanisms may lead to the initial tissue injury and precipitate synovial inflammation.

Clinical signs of synovitis may be subtle and are often subjective. Warm, swollen, obviously inflamed joints are usually seen only in the most active phases of inflammatory synovitis. Cartilage loss and erosion of periarticular bone are the characteristic features of structural damage. The clinical features related to structural damage are marked by progressive deterioration functionally and anatomically. Structural damage to the joint is irreversible and additive.

The effective treatment of rheumatoid arthritis has generally comprised a combination of medication, exercise, rest and proper joint protection therapy. The therapy for a particular patient depends on the severity of the disease and the joints that are involved. Non-steroidal anti-inflammatory drugs, corticosteroids, gold salts, methotrexate and systemic immunosuppressants are widely used to reduce inflammation and joint destruction. The use of steroids and immunosuppressants, however, has significant risks and side effects both in terms of toxicity and vulnerability to potentially lethal conditions. More recently therapeutics based on "biologicals" have been introduced into RA-therapy. Such therapeutics, e.g., are soluble receptors or antibodies directed against TNF-α that significantly reduce inflammation. Though very promising, biologicals are still in limited use due to high costs.

Data from longitudinal clinical and epidemiologic studies provide guidelines for treatment. These studies emphasize 1) the need for early diagnosis, 2) identification of prognostic factors, and 3) early aggressive treatment. Earlier diagnosis and treatment, preferably within the first several months after onset of symptoms, may help prevent irreversible joint damage.

Hence a need for methods, especially based on biochemical parameters, aiding in the assessment of rheumatoid arthritis exists. The present invention provides such methods and reagents for assessing the absence or presence of rheumatoid arthritis in vitro. The methods will also aid in monitoring the efficacy of treatment in patients suffering from RA.

DETAILED DESCRIPTION OF THE INVENTION

The present invention is directed to a method for assessing rheumatoid arthritis (RA) in vitro by biochemical markers, comprising measuring in a sample the concentration of anti-CCP and anti-PIK3CD and correlating the concentrations determined to the absence or presence of RA.

Further the present invention is directed to a method for assessing a severity of rheumatoid arthritis (RA) in vitro by biochemical markers, comprising measuring in a sample the concentration of anti-CCP and anti-PIK3CD, and correlating the concentrations to the severity of RA.

Also the present invention is directed to a method for differentiation of rheumatoid arthritis (RA) from other autoimmune diseases in vitro by biochemical markers, comprising measuring in a sample the concentration of anti-CCP and anti-PIK3CD and differentiating from an increased combined concentration value RA from other autoimmune diseases, preferably other joint diseases.

Further the use of a method to differentiate RA from other autoimmune diseases, preferably other joint diseases, is disclosed.

Further the use of a marker panel comprising anti-CCP and anti-PIK3CD for assessing the absence or presence of rheumatoid arthritis (RA) in vitro from a sample is disclosed.

Disclosed is further the use of an optimized multivariate cut-off for a marker panel comprising at least anti-CCP and anti-PIK3CD in assessing the absence or presence of RA, wherein said optimized multivariate cut-off is obtained by combining the concentration values measured for anti-CCP and anti-PIK3CD.

Also provided is a kit for performing the method according to the present invention comprising the reagents required to specifically measure anti-CCP and anti-PIK3CD, respectively, and optionally auxiliary reagents for performing the measurement.

In a first preferred embodiment the present invention relates to a method for assessing the absence or presence of rheumatoid arthritis (RA) in vitro by biochemical markers, comprising a) measuring in a whole blood, plasma or serum sample the concentration of at least anti-cyclic citrullinated peptides (anti-CCP) and anti-PIK3CD, respectively; b) combining the concentration values measured for anti-CCP and anti-PIK3CD in (a); and c) correlating a combined value determined in step (b) with the absence or presence of RA, wherein an increased combined value compared to the cut-off combined concentration value measured for anti-CCP and anti-PIK3CD from a reference population is indicative for the presence of RA.

In a second preferred embodiment the present invention relates to a method for assessing a severity of rheumatoid arthritis (RA) in vitro by biochemical markers, comprising a) measuring in a whole blood, plasma or serum sample the concentration of at least anti-cyclic citrullinated peptides (anti-CCP) and anti-PIK3CD, respectively; b) combining the concentration values measured for anti-CCP and anti-PIK3CD in (a); and c) correlating from an combined value from (b) to the severity of RA, wherein the higher the combined value compared to the cut-off combined concentration value measured for anti-CCP and anti-PIK3CD from a reference population is indicative for the severity of RA in the patient.

In a third preferred embodiment the present invention relates to a method for differentiation of rheumatoid arthritis (RA) from other autoimmune diseases in vitro by biochemical markers, comprising a) measuring in a whole blood, plasma or serum sample the concentration of at least anti-cyclic citrullinated peptides (anti-CCP) and anti-PIK3CD, respectively; b) combining the concentration values measured for anti-CCP and anti-PIK3CD in (a); and c) differentiating from an increased combined value from (b) RA from other autoimmune diseases, wherein an increased combined value compared to the cut-off combined concentration value measured for anti-CCP and anti-PIK3CD from a reference population is indicative for the presence of RA. Preferably, in one embodiment, the other autoimmune disease is osteoarthritis (OA).

As used herein, each of the following terms has the meaning associated with it in this section.

The articles "a" and "an" are used herein to refer to one or to more than one (i.e. to at least one) of the grammatical object of the article. By way of example, "a marker" means one marker or more than one marker.

The term "marker" or "biochemical marker" as used herein refers to a molecules to be used as a target for analyzing patient test samples. Examples of such molecular targets are proteins or polypeptides themselves as well as antibodies present in a sample. Proteins or polypeptides used as a marker in the present invention are contemplated to include any variants of said protein as well as fragments of said protein or said variant, in particular, immunologically detectable fragments. One of skill in the art would recognize that proteins which are released by cells or present in the extracellular matrix which become damaged, e.g., during inflammation could become degraded or cleaved into such fragments. Certain markers are synthesized in an inactive form, which may be subsequently activated by proteolysis. As the skilled artisan will appreciate, proteins or fragments thereof may also be present as part of a complex. Such complex also may be used as a marker in the sense of the present invention. Variants of a marker polypeptide are encoded by the same gene, but differ in their PI or MW, or both (e.g., as a result of alternative mRNA or pre-mRNA processing, e.g. alternative splicing or limited proteolysis) and in addition, or in the alternative, may arise from differential post-translational modification (e.g., glycosylation, acylation, and/or phosphorylation).

The term marker as indicated above according to the present invention also relates to antibodies present in a sample. In the case of RA these antibodies are autoantibodies, i.e. antibodies in a patient sample which bind to an antigen present in or on or produced by the patient's own cells.

The term "sample" as used herein refers to a biological sample obtained for the purpose of evaluation in vitro. In the methods of the present invention, the sample or patient sample preferably may comprise any body fluid. Preferred test samples include blood, serum, plasma, urine, saliva, and synovial fluid. Preferred samples are whole blood, serum or plasma, with plasma or serum being most preferred. Further preferred are samples from a human subject.

As the skilled artisan will appreciate, any such diagnosis is made in vitro. The patient sample is discarded afterwards. The patient sample is merely used for the in vitro diagnostic method of the invention and the material of the patient sample is not transferred back into the patient's body. Typically, the sample is a liquid sample.

The term "assessing rheumatoid arthritis" is used to indicate that the method according to the present invention will (together with other variables, e.g., the criteria set forth by the ARA (see above)) aid the physician to establish his diagnosis of RA. In a preferred embodiment this assessment will relate to the presence or absence of RA. As the skilled artisan will appreciate no biochemical marker is diagnostic with 100% specificity and at the same time 100% sensitivity for a given disease, rather biochemical markers are used to assess with a certain likelihood or predictive value the presence or absence of a disease. Preferably the method(s) according to the present invention aid in assessing the presence or absence of RA. In a further preferred embodiment the method(s) according to the present invention aid in detecting the presence or absence of RA. In a yet further preferred embodiment the method(s) according to the present invention aid in diagnosing the presence or absence of RA.

As the skilled artisan will appreciate the step of correlating a marker level to the presence or absence of RA can be performed and achieved in different ways. In general a reference population is selected and a normal range established. It is no more than routine experimentation, to establish the normal range for both anti-CCP as well as anti-PIK3CD using an appropriate reference population. It is generally accepted that the normal range to a certain but limited extent depends on the reference population in which it is established. The ideal reference population is high in number, e.g., hundreds to thousands, and matched for age, gender and optionally other variables of interest. The normal range in terms of absolute values, like a concentration given, also depends on the assay employed and the standardization used in producing the assay.

The levels for anti-CCP and anti-PIK3CD have been measured and established with the assay procedures given in the examples section. It has to be understood that different assays may lead to different cut-off values, without departing from the scope of the present invention.

Citrullinated peptides are antigens for rather important autoantibodies as found in the sera of patients with RA. They have been intensively studied during the past years by several groups of researchers (cf. e.g., WO 98/08946; WO 98/22503; WO 99/28344; WO 99/35167, WO 01/46222, and WO 03/050542). Recently Schellekens and co-workers (Schellekens, G. A. et al., Arthritis Rheum. 43 (2000) 155-163) reported that an ELISA-test based on specific cyclic citrullinated peptides (CCP) showed superior performance characteristics with regard to diagnostic accuracy for RA as compared to the same assay using linear peptides.

Auto-antibodies against CCP, i.e., antibodies which most likely are reactive with citrullinated polypeptides circulating in a patient serum and which bind to CCP in an in vitro assay are termed "anti-CCP". The patent application of van Venroji et al. (WO 98/22503) describes certain citrullinated peptides and shows that cyclization leads to an improved reactivity of the respective peptides. In a specific example it is shown that, if a peptide of the general formula HQCHQESTXGRSRGRCGRSGS (SEQ ID NO: 8), where X stands for citrulline, is cyclisized by a disulfide bond between the two cysteine residues, the sensitivity is increased to 63% as compared to 36% to the corresponding linear peptide. As autoantibodies in patient sera have slightly different reactivity to different cyclic peptides a combination of peptides was suggested in WO 98/22503 to further improve the assay.

In a preferred embodiment anti-CCP is measured as described by van Venroij et al in WO 03/050542. In brief, a combination of peptides that contain epitope sites with the general formula X-G and X-nonG wherein X stands for citrulline, G for glycine and nonG for any of the amino acids H, I, W, S, R, K, Y, M, F, V, P, Cit or an analogue thereof is used to assess the level of anti-CCP antibodies (anti-CCP) in a sample. Specific peptides useful in such assessment are disclosed in WO 03/050542. As the skilled artisan will readily appreciate, further improvements and refinements regarding the cyclic citrullinated peptide antigen used in an assay to measure anti-CCP are possible which will e.g. result in an altered sequence of the cyclic citrullinated peptide sequence. However, such modifications will not depart from the spirit of this invention.

The antibody binding to CCP, i.e., anti-CCP, is measured in a serological assay. Preferably such assay is set up by using one or more CCP as antigen and detecting the binding of anti-CCP antibodies comprised in a sample to the CCP antigen by appropriate means.

The MCM3 protein (minichromosome maintenance protein 3, Swiss Prot ID: P25205 (EC=3.6.4.12), SEQ ID NO: 5, is a 110 kD DNA-dependent ATPase containing a nuclear localization sequence. The MCM3 protein is a component of the DNA pre-replication complex that acts to allow DNA to undergo single round of replication per cell cycle. MCM3 is constitutively expressed and can be modified by acetylation. Acetylation of MCM3 inhibits the initiation of DNA replication. MCM3 has been reported to interact with the MCM5 (CDC46) and MCM3AP proteins.

Auto-antibodies against MCM3, i.e. antibodies which most likely are reactive with minichromosome maintenance protein 3 (MCM3) polypeptides circulating in a patient serum and which bind to MCM3 in an in vitro assay are termed "anti-MCM3".

The antibody binding to MCM3, i.e. anti-MCM3, is measured in a serological assay. Preferably such assay is set up by using one or more MCM3 as antigen and detecting the binding of anti-MCM3 antibodies comprised in a sample to the MCM3 antigen by appropriate means.

The Caspase-8 (Casp8) protein, SwissProt ID: Q14790 (EC:3.4.22.61), SEQ ID NO: 6, is a 55 kDa cytosolic protein that is synthesized as an inactive proenzyme. Activation of Casp8 involves a two-step proteolysis: the cleavage of Casp8 to generate a 43 kDa fragment and a 12 kDa which is further processed to 10 kDa, and then the p43 is then cleaved to yield p26 and the release of the active site containing p18.

Auto-antibodies against Casp8, i.e. antibodies which most likely are reactive with Caspase-8 (Casp8) polypeptides circulating in a patient serum and which bind to Casp8 in an in vitro assay are termed "anti-Casp8".

The antibody binding to Casp8, i.e. anti-Casp8, is measured in a serological assay. Preferably such assay is set up by using one or more Casp8 as antigen and detecting the binding of anti-Casp8 antibodies comprised in a sample to the Casp8 antigen by appropriate means.

The Phosphatidylinositol-4,5-bisphosphate 3-kinase catalytic subunit PI3-Kinase (PIK3CD) protein, SwissProt ID: O00329, SEQ ID NO: 7, belongs to the family of PI3-lipid kinases (PI3-Ks) that are implicated in signal transduction. PI3-K consists of two subunits; p85 and p110. The p85 subunit localize PI3-K activity to the plasma membrane while the p110 subunit contains the catalytic domain of PI3-K. Four isoforms of p110 has been found; the alpha, beta, gamma, and the delta subunit. The delta isoform is predominantly expressed in leukocytes and has been shown to interact with p85 and GTP-bound Ras via its SH2/SH3 domain.

Auto-antibodies against PIK3CD, i.e. antibodies which most likely are reactive with Phosphatidylinositol-4,5-bisphosphate 3-kinase catalytic subunit PI3-Kinase (PIK3CD) polypeptides circulating in a patient serum and which bind to PIK3CD in an in vitro assay are termed "anti-PIK3CD".

The antibody binding to PIK3CD, i.e. anti-PIK3CD, is measured in a serological assay. Preferably such assay is set up by using one or more PIK3CD as antigen and detecting the binding of anti-PIK3CD antibodies comprised in a sample to the PIK3CD antigen by appropriate means.

Preferred means of detection are specific binding assays, especially immunoassays. Immunoassays are well known to the skilled artisan. Methods for carrying out such assays as well as practical applications and procedures are summarized in related textbooks. Examples of related textbooks are Tijssen, P., In: Practice and theory of enzyme immunoassays, eds. R. H. Burdon and v. P. H. Knippenberg, Elsevier, Amsterdam (1990) 221-278 and various volumes of Methods in Enzymology, eds. S. P. Colowick, N. O. Caplan and S. P., Academic Press, dealing with immunological detection methods, especially volumes 70, 73, 74, 84, 92 and 121.

According to a further embodiment step (a) of the method(s) according to the present invention are performed by an immunoassay method.

In the method(s), preferably immunoassay method(s), according to the present invention anti-CCP is captured by one or more CCP as antigen.

In the method(s), preferably immunoassay method(s), according to the present invention anti-Casp8 is captured by one or more Casp8 as antigen.

In the method(s), preferably immunoassay method(s), according to the present invention anti-MCM3 is captured by one or more MCM3 as antigen.

In the method(s), preferably immunoassay method(s), according to the present invention anti-PIK3CD is captured by one or more PIK3CD as antigen.

In one embodiment the one or more capture antigen is either the full length protein or a polypeptide fragment selected from the protein.

In a preferred embodiment the capture antigen is CCP or a polypeptide fragment thereof.

In a preferred embodiment the capture antigen is Casp8 or a polypeptide fragment thereof.

In a preferred embodiment the capture antigen is MCM3 or a polypeptide fragment thereof.

In a preferred embodiment the capture antigen is PIK3CD or a polypeptide fragment thereof.

In a further embodiment the polypeptide fragment is an antigenic sequence of 10 to 25 AA selected from the protein.

In a yet further preferred embodiment the one or more capture antigen for anti-MCM3 is selected from SEQ ID NO: 5, respectively.

In a yet further preferred embodiment the one or more capture antigen for anti-Casp8 is selected from SEQ ID NO: 6, respectively.

In a yet further preferred embodiment the one or more capture antigen for anti-PIK3CD is selected from SEQ ID NO: 7, respectively.

In a yet further preferred embodiment the MCM3 capture antigen is peptide PATKKTIERRYSDLT (Y159, SEQ ID NO: 1).

In a yet further preferred embodiment the Casp8 capture antigen is peptide NKSLLKIINDYEEFS (Y178, SEQ ID NO: 2).

In a yet further preferred embodiment the PIK3CD capture antigen is peptide DQLKTGERCLYMWPS (Y440, SEQ ID NO: 3) and/or peptide DQLKTGERSLYMWPS (Y440*, SEQ ID NO: 4).

In an embodiment according to the method(s) of the present invention the one or more capture antigen is immobilized. Further, in one embodiment, the one or more capture antigen is immobilized on a solid support, preferably on a particle or bio-chip surface.

A "solid support" is insoluble, functionalized, polymeric material to which library members or reagents may be attached or covalently bound (often via a linker) to be immobilized or allowing them to be readily separated (by filtration, centrifugation, washing etc.) from excess reagents, soluble reaction by-products or solvents.

For anti-CCP, anti-PIK3CD, anti-Casp8 and anti-MCM3 the (auto-)antibodies as comprised in a sample are measured, respectively.

Anti-CCP antibodies may be detected by homogeneous assays formats, e.g., by agglutination of latex particles coated with CCP.

Preferably a heterogeneous immunoassay is used to measure anti-CCP. Such heterogeneous measurement is based on directly or indirectly coating CCP to a solid phase, incubating the solid phase with a sample known or suspected to comprise anti-CCP antibodies under conditions allowing for binding of anti-CCP antibodies to CCP, and directly or indirectly detecting the anti-CCP antibody bound. A further assay format is the so-called double antigen bridge assay, wherein, in case of an anti-CCP measurement, CCPs are used both at the solid phase side as well as at the detection side of this immunoassay and the autoantibodies in a patient sample form a bridge between these "double" antigens. Where necessary or appropriate, washing steps are included while performing a heterogeneous immunoassay.

In one embodiment according to the present invention antibody to cyclic citrullinated peptide (anti-CCP) is measured in an immunological assay, preferably an ELISA or electrochemiluminescence immunoassay (ECLIA).

According to the present invention antibody to cyclic citrullinated peptide (anti-CCP) in one specific embodiment is measured with the Elecsys Anti-CCP assay, which is commercial available. The anti-CP assay can for example be performed on Elecsys 2010, MODULAR ANALYTICS E170, cobas e 411, cobas e 601 or cobas e 602 analyzers (Example 2). In a specific embodiment according to the methods of the present invention the anti-CCP assay cut-off for RA positive is ≥5 U/mL. In a further specific embodiment the anti-CCP assay cut-off for RA negative is <5 U/mL.

Anti-Casp8 antibodies may be detected by homogeneous assays formats, e.g., by agglutination of latex particles coated with Casp8.

Preferably a heterogeneous immunoassay is used to measure anti-Casp8. Such heterogeneous measurement is based on directly or indirectly coating Casp8 to a solid phase, incubating the solid phase with a sample known or suspected to comprise anti-Casp8 antibodies under conditions allowing for binding of anti-Casp8 antibodies to Casp8, and directly or indirectly detecting the anti-Casp8 antibody bound. A further assay format is the so-called double antigen bridge assay, wherein, in case of an anti-Casp8 measurement, Casp8s are used both at the solid phase side as well as at the detection side of this immunoassay and the autoantibodies in a patient sample form a bridge between these "double" antigens. Where necessary or appropriate, washing steps are included while performing a heterogeneous immunoassay.

In one embodiment according to the present invention antibody to Caspase-8 (anti-Casp8) is measured in an immunological assay, preferably an ELISA or electrochemiluminescence immunoassay (ECLIA).

For the reference population as shown in Example 1 and Table 1 and the methods according to the present invention a cut-off for the marker anti-[Casp8] of 49.9 U/mL was selected.

In a specific embodiment the anti-Casp8 assay cut-off for RA positive is ≥49.9 U/mL. In a further specific embodiment the anti-Casp8 assay cut-off for RA negative is <49.9 U/mL.

Anti-MCM3 antibodies may be detected by homogeneous assays formats, e.g., by agglutination of latex particles coated with MCM3.

Preferably a heterogeneous immunoassay is used to measure anti-MCM3. Such heterogeneous measurement is based on directly or indirectly coating MCM3 to a solid phase, incubating the solid phase with a sample known or suspected to comprise anti-MCM3 antibodies under conditions allowing for binding of anti-MCM3 antibodies to MCM3, and directly or indirectly detecting the anti-MCM3 antibody bound. A further assay format is the so-called double antigen bridge assay, wherein, in case of an anti-MCM3 measurement, MCM3 are used both at the solid phase side as well as at the detection side of this immunoassay and the autoantibodies in a patient sample form a bridge between these "double" antigens. Where necessary or appropriate, washing steps are included while performing a heterogeneous immunoassay.

In one embodiment according to the present invention antibody to minichromosome maintenance protein 3 (anti-MCM3) is measured in an immunological assay, preferably an ELISA or electrochemiluminescence immunoassay (ECLIA).

For the reference population as shown in Example 1 and Table 1 and the methods according to the present invention a cut-off for the marker anti-MCM3 of 15.1 U/mL was selected.

In a specific embodiment the anti-MCM3 assay cut-off for RA positive is ≥15.1 U/mL. In a further specific embodiment the anti-MCM3 assay cut-off for RA negative is <15.1 U/mL.

Anti-PIK3CD antibodies may be detected by homogeneous assays formats, e.g., by agglutination of latex particles coated with PIK3CD.

Preferably a heterogeneous immunoassay is used to measure anti-PIK3CD. Such heterogeneous measurement is based on directly or indirectly coating PIK3CD to a solid phase, incubating the solid phase with a sample known or suspected to comprise anti-PIK3CD antibodies under conditions allowing for binding of anti-PIK3CD antibodies to PIK3CD, and directly or indirectly detecting the anti-PIK3CD antibody bound. A further assay format is the so-called double antigen bridge assay, wherein, in case of an anti-PIK3CD measurement, PIK3CD are used both at the solid phase side as well as at the detection side of this immunoassay and the autoantibodies in a patient sample form a bridge between these "double" antigens. Where necessary or appropriate, washing steps are included while performing a heterogeneous immunoassay.

In one embodiment according to the present invention antibody to Phosphatidylinositol-4,5-bisphosphate 3-kinase catalytic subunit PI3-Kinase (anti-PIK3CD) is measured in an immunological assay, preferably an ELISA or electrochemiluminescence immunoassay (ECLIA).

For the reference population as shown in Example 1 and Table 1 and the methods according to the present invention a cut-off for the marker anti-PIK3CD of 15.1 U/mL was selected.

In a specific embodiment the anti-PIK3CD assay cut-off for RA positive is ≥15.1 U/mL. In a further specific embodiment the anti-PIK3CD assay cut-off for RA negative is <15.1 U/mL.

The ideal scenario for diagnosis would be a situation wherein a single event or process would cause the respective disease as, e.g., in infectious diseases. In all other cases correct diagnosis can be very difficult, especially when the etiology of the disease is not fully understood as is the case for RA. Therefore, generally various clinical symptoms and biological markers are considered together for diagnosis of RA. Markers can either be determined individually or in a preferred embodiment of the invention they can be measured simultaneously using a chip (bio-chip) or a bead based array technology. The concentrations of the biomarkers are then interpreted independently using an individual cut-off for each marker or they are combined for interpretation.

In a preferred embodiment of the present invention the combined concentration values of step (b) are compared to a cut-off value derived from a reference population excluding RA-positive patients, comprising obviously healthy and patients selected from the group consisting of osteoarthritis (OA) patients and other autoimmune disease patients.

Marker panels in one embodiment are combined within a single test device, e.g. on a chip or in an array format. A marker panel according to the present invention is in an embodiment determined using a bio-chip array (protein array) technique. An array is a collection of addressable individual markers. Such markers can be spacially addressable, such as arrays contained within microtiter plates or printed on planar surfaces where each marker is present at distinct X and Y coordinates. Alternatively, markers can be addressable based on tags, beads, nanoparticles, or physical properties. A bio-chip array can be prepared according to the methods known to the ordinarily skilled artisan (see for example, U.S. Pat. No. 5,807,522; Robinson, W. H., et al., Nat. Med. 8 (2002) 295-301; Robinson, W. H., et al., Arthritis Rheum. 46 (2002) 885-893). Array as used herein refers to any immunological assay with multiple addressable markers. A bio-chip array, also known to the skilled artisan as microarray, is a miniaturized form of an array.

The terms "chip", "bio-chip", "polymer-chip" or "protein-chip" are used interchangeably and refer to a collection of a large number of probes, markers or biochemical markers arranged on a shared substrate which could be a portion of a silicon wafer, a nylon strip, a plastic strip, or a glass slide.

An "array," "macroarray" or "microarray" is an intentionally created collection of substances, such as molecules, markers, openings, microcoils, detectors and/or sensors, attached to or fabricated on a substrate or solid surface, such as glass, plastic, silicon chip or other material forming an array. The arrays can be used to measure the levels of large numbers, e.g., tens, thousands or millions, of reactions or combinations simultaneously. An array may also contain a small number of substances, e.g., one, a few or a dozen. The substances in the array can be identical or different from each other. The array can assume a variety of formats, e.g., libraries of soluble molecules, libraries of immobilized molecules, libraries of immobilized antibodies, libraries of compounds tethered to resin beads, silica chips, or other solid supports. The array could either be a macroarray or a microarray, depending on the size of the pads on the array. A macroarray generally contains pad sizes of about 300 microns or larger and can be easily imaged by gel and blot scanners. A microarray would generally contain pad sizes of less than 300 microns.

In an embodiment the present invention relates to a bio-chip array comprising the immobilized capture antigen CCP and at least one or more immobilized capture antigen selected from the group consisting of anti-PIK3CD, anti-MCM3 and anti-Casp8.

The present invention also provides in an embodiment a bio-chip array for performing the method according to the present invention to specifically determine the concentration of anti-CCP and of at least one or more marker selected from the group consisting of anti-PIK3CD, anti-MCM3 and anti-Casp8, and optionally auxiliary reagents for performing the measurement.

The present invention also provides in an embodiment a bio-chip array for performing the method according to the present invention to specifically determine the concentration of anti-CCP and of at least one or more marker selected from the group consisting of anti-PIK3CD, anti-MCM3 and anti-Casp8, and optionally auxiliary reagents in the assessment of the presence or absence of RA.

As shown in the examples section the mere combination of the two markers anti-CCP and anti-Casp8 significantly improves the diagnostic accuracy for RA.

In a method according to the present invention at least the concentration of the biomarkers anti-CCP and anti-PIK3CD, respectively, is determined and the marker combination is correlated to the absence or presence of RA.

As the skilled artisan will appreciate there are many ways to use the measurements of two or more markers in order to improve the diagnostic question under investigation. In a quite simple, but nonetheless often effective approach, a positive result is assumed if a sample is positive for at least one of the markers investigated. This may e.g. the case when diagnosing an infectious disease, like AIDS. Frequently, however, the combination of markers is evaluated.

Preferably the values measured for markers of a marker panel, e.g. for anti-CCP and anti-PIK3CD, are mathematically combined and the combined value is correlated to the underlying diagnostic question. Marker values may be combined by any appropriate state of the art mathematical method. Well-known mathematical methods for correlating a marker combination to a disease employ methods like, discriminant analysis (DA) (i.e. linear-, quadratic-, regularized-DA), Kernel Methods (i.e. SVM), Nonparametric Methods (i.e. k-Nearest-Neighbor Classifiers), PLS (Partial Least Squares), Tree-Based Methods (i.e. Logic Regression, CART, Random Forest Methods, Boosting/Bagging Methods), Generalized Linear Models (i.e. Logistic Regression), Principal Components based Methods (i.e. SIMCA), Generalized Additive Models, Fuzzy Logic based Methods, Neural Networks and Genetic Algorithms based Methods. The skilled artisan will have no problem in selecting an appropriate method to evaluate a marker combination of the present invention. Preferably the method used in correlating the marker combination of the invention e.g. to the absence or presence of RA is selected from DA (i.e. Linear-, Quadratic-, Regularized Discriminant Analysis), Kernel Methods (i.e. SVM), Nonparametric Methods (i.e. k-Nearest-Neighbor Classifiers), PLS (Partial Least Squares), Tree-Based Methods (i.e. Logic Regression, CART, Random Forest Methods, Boosting Methods), or Generalized Linear Models (i.e. Logistic Regression). Details relating to these statistical methods are found in the following references: Ruczinski, I., Kooperberg C., LeBlanc, M., Logic regression, J. of Computational and Graphical Statistics, 12 (2003) 475-511; Friedman, J. H., Regularized Discriminant Analysis, J. of the American Statistical Association, Vol. 84 (1989) 165-175; Hastie, Trevor, Tibshirani, Robert, Friedman, Jerome, The Elements of Statistical Learning, Springer Series in Statistics, 2001; Breiman, L., Friedman, J. H., Olshen, R. A., Stone, C. J. (1984) Classification and regression trees, California: Wadsworth; Breiman, L., Random Forests, Machine Learning, 45 (2001) 5-32; Pepe, M. S., The Statistical Evaluation of Medical Tests for Classification and Prediction, Oxford Statistical Science Series, 28 (2003); and Duda, R. O., Hart, P. E., Stork, D. G., Pattern Classification, Wiley Interscience, 2nd Edition (2001).

In a preferred embodiment the method(s) according to the method the present invention the concentration values measured in step (b) are combined mathematically by using a member selected from the group consisting of Discriminant analysis, Kernel Methods, Nonparametric Methods, Partial Least Squares, Tree-Based Methods, Generalized Linear Models, Principal Components based Methods, Generalized Additive Models, Fuzzy Logic based Methods, Neural Networks and Genetic Algorithms based Methods.

It is a preferred embodiment of the invention to use an optimized multivariate cut-off for the underlying combination of biological markers and to discriminate state A from state B, e.g. diseased from healthy. In this type of analysis the markers are no longer independent but form a marker panel. It could be established that combining the measurements of anti-CCP and of anti-PIK3CD does significantly improve the diagnostic accuracy for RA as compared to either healthy controls or, as also assessed, as compared to patients with osteoarthritis (OA). Especially the later finding is of great importance, because patients with OA and RA, respectively, may require quite different treatments.

Accuracy of a diagnostic method is best described by its receiver-operating characteristics (ROC) (see especially Zweig, M. H., and Campbell, G., Clin. Chem. 39 (1993) 561-577). The ROC graph is a plot of all of the sensitivity/specificity pairs resulting from continuously varying the decision thresh-hold over the entire range of data observed.

The clinical performance of a laboratory test depends on its diagnostic accuracy, or the ability to correctly classify subjects into clinically relevant subgroups. Diagnostic accuracy measures the test's ability to correctly distinguish two different conditions of the subjects investigated. Such conditions are for example health and disease or benign versus malignant disease.

In each case, the ROC plot depicts the overlap between the two distributions by plotting the sensitivity versus 1−specificity for the complete range of decision thresholds. On the y-axis is sensitivity, or the true-positive fraction [defined as (number of true-positive test results)/(number of true-positive+number of false-negative test results)]. This has also been referred to as positivity in the presence of a disease or condition. It is calculated solely from the affected subgroup. On the x-axis is the false-positive fraction, or 1−specificity [defined as (number of false-positive results)/(number of true-negative+number of false-positive results)]. It is an index of specificity and is calculated entirely from the unaffected subgroup. Because the true- and false-positive fractions are calculated entirely separately, by using the test results from two different subgroups, the ROC plot is independent of the prevalence of disease in the sample. Each point on the ROC plot represents a sensitivity/1−specificity pair corresponding to a particular decision threshold. A test with perfect discrimination (no overlap in the two distributions of results) has an ROC plot that passes through the upper left corner, where the true-positive fraction is 1.0, or 100% (perfect sensitivity), and the false-positive fraction is 0 (perfect specificity). The theoretical plot for a test with no discrimination (identical distributions of results for the two groups) is a 45° diagonal line from the lower left corner to the upper right corner. Most plots fall in between these two extremes. (If the ROC plot falls completely below the 45° diagonal, this is easily remedied by reversing the criterion for "positivity" from "greater than" to "less than" or vice versa.) Qualitatively, the closer the plot is to the upper left corner, the higher the overall accuracy of the test.

One convenient goal to quantify the diagnostic accuracy of a laboratory test is to express its performance by a single number. The most common global measure is the area under the ROC plot. By convention, this area is always >0.5 (if it is not, one can reverse the decision rule to make it so). Values range between 1.0 (perfect separation of the test values of the two groups) and 0.5 (no apparent distributional difference between the two groups of test values). The area does not depend only on a particular portion of the plot such as the point closest to the diagonal or the sensitivity at 90% specificity, but on the entire plot. This is a quantitative, descriptive expression of how close the ROC plot is to the perfect one (area=1.0).

In a preferred embodiment the present invention relates to a method for improving the diagnostic accuracy for rheumatoid arthritis versus healthy controls and/or patients suffering from OA by measuring in a sample the concentration of at least anti-CCP and anti-PIK3CD and correlating the concentrations determined to the presence or absence of rheumatoid arthritis, the improvement resulting in more patients being correctly classified as suffering from RA versus healthy controls and/or patients suffering from OA as compared to a classification based on anti-CCP alone. The RA marker panel comprising anti-CCP and anti-PIK3CD can of course also be used in assessing the severity of disease for patients suffering from RA.

As the skilled artisan will appreciate one or more additional biomarker may be used to further improve the assessment of RA. To illustrate this additional potential of using anti-CCP and anti-PIK3CD as the key markers of a panel of markers for assessment of RA the term "at least" has been used in the appending claims. With other words, the level measured for one or more additional marker may be combined with the measurement of anti-CCP and anti-PIK3CD in the assessment of RA.

The one or more additional marker used together with anti-CCP and anti-PIK3CD may be considered to be part of an RA marker panel, i.e., a series of markers appropriate to further refine the assessment of RA. The total number of markers in an RA marker panel is preferably less than 20 markers, more preferred less than 15 markers, also preferred are less than 10 markers with 8 or less markers being even more preferred. Preferred are RA marker panels comprising 3, 4, 5, or 6 markers in total.

In a preferred embodiment the present invention thus relates to a method for assessing the absence or presence of rheumatoid arthritis in vitro by biochemical markers, comprising measuring in a sample the concentration of anti-CCP, anti-PIK3CD and in addition the concentration of one or more other marker and correlating the concentrations of anti-CCP, anti-PIK3CD and of the one or more additional marker to the absence or presence of RA.

It will be appreciated that the one or more other marker may be combined with any known or future marker of RA. A marker does qualify as an RA marker if the AUC for this marker alone, when assessing the diagnostic accuracy by comparing patients with RA to healthy controls, is at least 0.65.

Preferably, in an embodiment, the one or more other marker is selected from the group consisting of anti-MCM3 and anti-PIK3CD.

A feature of rheumatoid arthritis is the invasion of joints with proliferating synovial tissue also known as pannus. A significant part of the pannus consists of blood vessels that supplies nutrients to the growing tissue. Therefore, molecules relevant in angiogenesis have been investigated in RA also, both as RA markers but also as therapeutic targets (Brenchley, P. E. C., Clin. Exp. Immunol. 121 (2000) 426-429). Amongst these the vascular endothelial growth factor (=VEGF) has been evaluated in more detail. VEGF is a secreted glycoprotein that is spliced to four different isoforms. Two of these isoforms are readily diffusible while the remaining isoforms bind tightly to heparin and are mostly found in association with heparin containing proteoglycans. VEGF acts as a chemokine on endothelial cells, monocytes and osteoblasts ultimately leading to neovascularization and increased microvascular permeability. VEGF has been detected in synovial fluid and serum of RA patients (Lee, S. S., et al., Clin. Exp. Rheumathology 19 (2001) 321-324; Ballara, S., Arthritis Rheum. 44 (2001) 2055-2064). Preferably, the marker of angiogenesis is VEGF.

The most prominent joint tissues are bone, cartilage and the synovium. Since rheumatoid arthritis is a destructive disease these tissues will be most affected. They are a likely source of potential biological markers in the field of RA. In principle these markers may come not only from the destruction of the respective tissue but also from a deregulated and/or ineffective repair process. The experienced artisan will understand that markers of bone, cartilage or synovium metabolism can originate either from synthesis or from destruction of these tissues. The various markers of bone, cartilage and/or synovium metabolism can be delineated from two different groups of proteins. They come either from the numerous types of collagen or from non-collagenous proteins. Non-collagenous proteins are often involved in the formation of the extracellular matrix. Some of these markers can be found in all three tissues in varying amounts.

Preferably the RA marker panel comprises at least three markers, wherein anti-CCP, anti-PIK3CD and a third marker selected from the group consisting anti-MCM3 and anti-Casp8 are contained.

In the assessment of RA a marker panel comprising anti-CCP, anti-PIK3CD, anti-MCM3 and anti-Casp8 is preferred.

A further preferred panel of RA markers comprises anti-CCP, anti-PIK3CD and anti-MCM3.

A further preferred panel of RA markers comprises anti-CCP, anti-PIK3CD and anti-Casp8.

Also preferred the at least one additional marker is selected from the group consisting of anti-MCM3 and anti-Casp8. In a further preferred embodiment the additional marker is anti-MCM3. In a further preferred embodiment the additional marker is anti-Casp8.

As mentioned further above (see ARA criteria)—despite severe limitations—the rheumatoid factor (RF) currently is the only biochemical marker generally accepted to aid in establishing the diagnosis of RA. It is clearly expected that the marker combination of the present invention will significantly improve the diagnosis of RA and will supplement or might be even finally replace the RF assay. The use of a marker panel comprising at least anti-CCP and anti-PIK3CD in the diagnosis of RA therefore represents a further preferred embodiment of the present invention.

As the skilled artisan will appreciate one or more additional marker may be used to further improve the diagnostic accuracy, or, where required increase the diagnostic sensitivity at the expense of specificity or vice versa. In some diagnostic areas, e.g., in the detection of an HIV-infection sensitivity is of utmost importance. The high sensitivity required may be achieved at the expense of specificity, leading to an increased number of false positive cases. In other cases, e.g. as a simple example, when assessing blood group antigens, specificity is of paramount importance.

A further preferred embodiment relates to the use of a marker panel in the diagnosis of RA the panel comprising anti-CCP, anti-PIK3CD and at least one additional marker selected from the group consisting of anti-MCM3 and anti-PIK3CD.

Preferably an embodiment relates to the use of a marker panel comprising at least anti-CCP and anti-PIK3CD for assessing the absence or presence of rheumatoid arthritis (RA) in vitro from a whole blood, plasma or serum sample, wherein an increased combined concentration value measured for anti-CCP and anti-PIK3CD compared to the cut-off combined concentration value measured for anti-CCP and anti-PIK3CD from a reference population is indicative for the presence of RA.

In a further embodiment the use of a marker panel further comprises anti-CCP, anti-PIK3CD and at least one additional marker selected from the group consisting of anti-MCM3 and anti-Casp8. Preferably the marker panel comprises anti-CCP, anti-PIK3CD and anti-MCM3. Also preferably the marker panel comprises anti-CCP, anti-PIK3CD and anti-Casp8.

The method according to the present invention will also be of great use in assessing the severity of RA. The higher the level of anti-CCP and/or the higher the level of anti-PIK3CD the more severe is the disease. With the marker combination or marker panels now at hand it will be no more than routine experimentation to develop e.g., disease scores as an indicator for severity of disease. The method according to the present invention thus is preferably also used to assess the severity of disease.

The method according to the present invention will also be of great use to differentiate RA from other autoimmune diseases, preferably other joint diseases, even more preferably the other joint disease is osteoarthritis (OA).

The invention further relates in an embodiment to the use of an optimized multivariate cut-off for a marker panel comprising at least anti-CCP and anti-PIK3CD in assessing the absence or presence of RA, wherein said optimized multivariate cut-off is obtained by combining the concentration values measured for anti-CCP and anti-PIK3CD. Preferably the concentration values measured are combined mathematically by using a member selected from the group consisting of Discriminant analysis, Kernel Methods, Non-parametric Methods, Partial Least Squares, Tree-Based Methods, Generalized Linear Models, Principal Components based Methods, Generalized Additive Models, Fuzzy Logic based Methods, Neural Networks and Genetic Algorithms based Methods.

The method of the present invention will also be of great help in monitoring the course of disease. This is most easily achieved by measuring in a patient sample anti-CCP and anti-PIK3CD as well as optionally additional markers at various points in time and comparing the absolute and/or the relative levels of the markers at these different time points. It thus is further preferred to use the method according to the present invention to monitor the course of disease in a patient with RA.

It is also recognized that the present invention will be of great help in assessing the efficacy of any treatment for RA. The efficacy of treatment will be reflected by changes in the marker level. If a treatment has the desired effect at least one of the two marker levels of anti-CCP or anti-PIK3CD will decrease. The method according to the present invention thus preferably is also used to assess the efficacy of treatment. The same phenomenon, i.e. a reduction in marker level of at least one of anti-CCP or anti-PIK3CD can easily be applied for selection of the right drug as well as the most appropriate dosing of drugs in RA. The use of a method of this invention in selection of the right drug and/or the most appropriate dosing is also preferred.

The method of the present invention will also enable the selection and identification of new drugs in the field of RA. This application represents a further preferred embodiment.

It will also be a great advantage that sub-groups of patients can now be identified for and in clinical studies which differ in their level of anti-CCP and anti-PIK3CD and to correlate this difference in marker level to the efficacy of the drug under investigation.

The present invention also relates to a kit for performing the method of this invention comprising the reagents required to specifically measure anti-CCP and anti-PIK3CD, respectively. The kit may optionally comprise auxiliary reagents for performing the measurement of both anti-CCP and anti-PIK3CD.

In a specific embodiment the kit comprises the reagents to specifically measure the concentration of anti-CCP and anti-PIK3CD.

In a preferred embodiment the kit comprises peptides selected from the group consisting of CCP, MCM3, Casp8 and PIK3CD, respectively, depending on the auto-antibodies to be determined.

In a further preferred embodiment the capture antigens in the kit are selected from the group consisting of peptide PATKKTIERRYSDLT (Y159, SEQ ID NO: 1) for the detection of anti-MCM3, of peptide NKSLLKIINDYEEFS (Y178, SEQ ID NO: 2) for the detection of anti-Casp8 and of peptide DQLKTGERCLYMWPS (Y440, SEQ ID NO: 3) and/or peptide DQLKTGERSLYMWPS (Y440*, SEQ ID NO: 4) for the detection of PIK3CD, respectively, depending on the auto-antibodies to be determined.

In a further preferred embodiment the specific capture peptide is immobilized on a solid support.

In an embodiment according to the present invention the solid support is a bead, preferably a magnetic bead or a bio-chip surface.

Further optional features and embodiments of the invention will be disclosed in more detail in the subsequent description of preferred embodiments, preferably in conjunction with the dependent claims. Therein, the respective optional features may be realized in an isolated fashion as well as in any arbitrary feasible combination, as the skilled person will realize. The scope of the invention is not restricted by the preferred embodiments.

Summarizing the findings of the present invention, the following embodiments are preferred:

1. A method for assessing the absence or presence of rheumatoid arthritis (RA) in vitro by biochemical markers, comprising
   a) measuring in a whole blood, plasma or serum sample the concentration of at least anti-cyclic citrullinated peptides (anti-CCP) and anti-PIK3CD, respectively;
   b) combining the concentration values measured for anti-CCP and anti-PIK3CD in (a); and
   c) correlating a combined value determined in step (b) with the absence or presence of RA, wherein an increased combined value compared to the cut-off combined concentration value measured for anti-CCP and anti-PIK3CD from a reference population is indicative for the presence of RA.
2. The method according to claim 1, wherein the sample is from a human subject.
3. The method according any one of claims 1 to 2, wherein step (a) of the method is an immunoassay method.
4. The method according to claim 3, wherein anti-CCP and anti-PIK3CD are captured by one or more CCP as antigen and/or one or more PIK3CD as antigen, respectively.
5. The method according to claim 4, wherein the one or more capture antigen is immobilized.
6. The method according to claim 5, wherein the one or more capture antigen is immobilized on a solid support, preferably on a particle or bio-chip surface.
7. The method according to any one of claims 4 and 6, wherein the one or more capture antigen is either the full length protein or a polypeptide fragment selected from the protein.
8. The method according to claim 7, wherein polypeptide fragment is an antigenic sequence of 10 to 25 AA selected from the protein.
9. The method according to any of the claims 4 to 8, wherein the one or more capture antigen for marker anti-PIK3CD is selected from SEQ ID NO: 7.
10. The method according to claim 9, wherein the PIK3CD capture antigen for marker anti-PIK3CD is peptide DQLKTGERCLYMWPS (Y440, SEQ ID NO: 3) and/or peptide DQLKTGERSLYMWPS (Y440*, SEQ ID NO: 4).
11. The method according to any one of the claims 1 to 10, wherein the combined concentration values of step (b) are compared to a cut-off value derived from a reference population excluding RA-positive patients, comprising obviously healthy and patients selected from the group consisting of osteoarthritis (OA) patients and other autoimmune disease patients.
12. The method according to any one of the claims 1 to 11, wherein the concentration values measured in step (b) are combined mathematically by using a member selected from the group consisting of Discriminant analysis, Kernel Methods, Nonparametric Methods, Partial Least Squares, Tree-Based Methods, Generalized Linear Models, Principal Components based Methods, Generalized Additive Models, Fuzzy Logic based Methods, Neural Networks and Genetic Algorithms based Methods.
13. The method according to any one of the claims 1 to 12, further comprising the measurement of at least one additional marker selected from the group consisting of anti-MCM3 and anti-Casp8.
14. The method according to claim 13, wherein the additional marker is anti-MCM3.
15. The method according to claim 14, wherein the MCM3 capture antigen for marker anti-MCM3 is peptide PATKKTIERRYSDLT (Y159, SEQ ID NO: 1)
16. The method according to claim 13, wherein the additional marker is anti-Casp8.
17. The method according to claim 16, wherein the Casp8 capture antigen for marker anti-Casp8 is peptide NKSLLKIINDYEEFS (Y178, SEQ ID NO: 2).
18. A method for assessing a severity of rheumatoid arthritis (RA) in vitro by biochemical markers, comprising
   a) measuring in a whole blood, plasma or serum sample the concentration of at least anti-cyclic citrullinated peptides (anti-CCP) and anti-PIK3CD, respectively;
   b) combining the concentration values measured for anti-CCP and anti-PIK3CD in (a); and
   c) correlating from an combined value from (b) to the severity of RA, wherein the higher the combined value compared to the cut-off combined concentration value measured for anti-CCP and anti-PIK3CD from a reference population is indicative for the severity of RA in the patient.
19. A method for differentiation of rheumatoid arthritis (RA) from other autoimmune diseases in vitro by biochemical markers, comprising a) measuring in a whole blood, plasma or serum sample the concentration of at least anti-cyclic citrullinated peptides (anti-CCP) and anti-PIK3CD, respectively;
b) combining the concentration values measured for anti-CCP and anti-PIK3CD in (a); and
c) differentiating from an increased combined value from (b) RA from other autoimmune diseases, wherein an increased combined value compared to the cut-off combined concentration value measured for anti-CCP and anti-PIK3CD from a reference population is indicative for the presence of RA.

20. The method according to claim 19, wherein the other autoimmune disease is osteoarthritis (OA).
21. Use of a marker panel comprising at least anti-CCP and anti-PIK3CD for assessing the absence or presence of rheumatoid arthritis (RA) in vitro from a whole blood, plasma or serum sample, wherein an increased combined concentration value measured for anti-CCP and anti-PIK3CD compared to the cut-off combined concentration value measured for anti-CCP and anti-PIK3CD from a reference population is indicative for the presence of RA.
22. The use according to claim 21, wherein the marker panel further comprises anti-CCP, anti-PIK3CD and at least one additional marker selected from the group consisting of anti-MCM3 and anti-Casp8.
23. The use according to claim 21, wherein the marker panel comprises anti-CCP, anti-PIK3CD and anti-MCM3.
24. The use according to claim 21, wherein the marker panel comprises anti-CCP, anti-PIK3CD and anti-Casp8.
25. Use of the method according to claim 19 to differentiate RA from other autoimmune diseases, preferably other joint diseases.
26. The use according to claim 25, wherein the other joint disease is osteoarthritis (OA).
27. Use of an optimized multivariate cut-off for a marker panel comprising at least anti-CCP and anti-PIK3CD in assessing the absence or presence of RA, wherein said optimized multivariate cut-off is obtained by combining the concentration values measured for anti-CCP and anti-PIK3CD.
28. The use according to claim 27 wherein the concentration values measured are combined mathematically by using a member selected from the group consisting of Discriminant analysis, Kernel Methods, Nonparametric Methods, Partial Least Squares, Tree-Based Methods, Generalized Linear Models, Principal Components based Methods, Generalized Additive Models, Fuzzy Logic based Methods, Neural Networks and Genetic Algorithms based Methods.
29. A kit for performing the method according to any one of the claims 1 to 20 comprising the reagents required to specifically measure anti-CCP and anti-PIK3CD, respectively, and optionally auxiliary reagents for performing the measurement.

The following examples, references, sequence listing and figures are provided to aid the understanding of the present invention, the true scope of which is set forth in the appended claims. It is understood that modifications can be made in the procedures set forth without departing from the spirit of the invention.

Description of Sequences
SEQ ID NO: 1 MCM3 peptide PATKKTIERRYSDLT (Y159) used to capture anti-MCM3
SEQ ID NO: 2 Casp8 peptide NKSLLKIINDYEEFS (Y178) used to capture anti-Casp8
SEQ ID NO: 3 PIK3CD peptide DQLKTGERCLYMWPS (Y440) used to capture anti-PIK3CD
SEQ ID NO: 4 PIK3CD peptide DQLKTGERSLYMWPS (Y440*) used to capture anti-PIK3CD. For technical reasons, cysteines (C) of SEQ ID NO: 3 was replaced by serines (S) in SEQ ID NO: 4
SEQ ID NO: 5 Minichromosome maintenance protein 3 (MCM3) human protein, SwissProt ID: P25205
SEQ ID NO: 6 Caspase-8 (Casp8) human protein, SwissProt ID: Q14790
SEQ ID NO: 7 Phosphatidylinositol-4,5-bisphosphate 3-kinase catalytic subunit PI3-Kinase (PIK3CD) human protein, SwissProt ID: O00329
SEQ ID NO: 8 Anti-CCP peptide HQCHQESTXGRSR-GRCGRSGS of WO 98/22503, where X stands for citrulline; peptide cyclisized by a disulfide bond between the two cysteine residues.

Example 1

Study Population

Samples derived from 78 highly characterized RA patients with maximum disease duration of 15 years were collected in five European centers with a follow-up of two years. 53 of the RA patients were anti-CCP negative. All individuals were diagnosed as RA-patients according to the ARA-criteria and had a functional status of ≤III as classified by the ARA classification criteria (Hochberg, M. C., et al., Arthritis Rheum. 35 (1992) 498-502). All patients were documented with an extensive case report form (=CRF). The CRF included the Health Assessment Questionnaire, the SF36 Questionnaire, swollen and tender joint count, the Larsen Score, laboratory parameters, clinical history of relevant surgery, medication, co-morbidities and medication for co-morbidities. X-rays were taken every year following a standardized procedure. Only baseline samples obtained from the subjects included in this study were included in the present analysis.

Samples derived from 89 control subjects were collected as well. From these controls only RA-positive subjects but no other forms of arthritis were excluded. Since the focus of the study was to discriminate RA not only from healthy subjects but also from other joint diseases, 40 patients with either tibiofemoral or patellofemoral OA of the knee were added as disease controls. For these OA patients clinical and laboratory parameters were determined and radiographic Kellgren & Lawrence Score was calculated (Kellgren, J. H., and Lawrence, J. S., Ann. Rheum. Dis. 16 (1957) 494-502).

Demographic data for the study population are given in Table 1.

TABLE 1

| Patient collectives | | | |
|---|---|---|---|
| Collective | N | median age | gender (f/m) |
| RA - anti-CCP pos. | 25 | 63 | 19/6 |
| RA - anti-CCP neg. | 53 | 63 | 36/17 |
| OA | 40 | 59 | 29/11 |
| Other autoimmune diseases | 49 | 51 | 23/26 |

Example 2

Anti-CCP Assay

A commercial available anti-CCP electrochemiluminescence immunoassay (ECLIA) for use on Elecsys® or Cobas® e immunoassay analyzers (e.g. Elecsys 2010, MODULAR ANALYTICS E170, cobas e 411, cobas e 601 or cobas e 602) with the order No. 05 031 656 190 was selected to determine CCP autoantibodies in samples.

The Immunoassay is for the in vitro semi-quantitative determination of human IgG autoantibodies to cyclic citrullinated peptides in human serum and plasma. The results of the assay are intended to be used as an aid in the diagnosis of rheumatoid arthritis in combination with other clinical and laboratory findings.

Test Principle:

First incubation: 15 µL of sample are incubated with biotinylated cyclic citrullinated peptides and ruthenylated (Tris(2,2'-bipyridyl)ruthenium(II)-complex (Ru(bpy)$^{2+}_3$)) monoclonal antibody against human IgG, forming a complex when CCP-specific antibodies are present in the sample.

Second incubation: After addition of streptavidin-coated microparticles, the complex becomes bound to the solid phase via interaction of biotin and streptavidin.

The reaction mixture is aspirated into the measuring cell where the microparticles are magnetically captured onto the surface of the electrode. Unbound substances are then removed with ProCell/ProCell M. Application of a voltage to the electrode then induces chemiluminescent emission which is measured by a photomultiplier.

Results are determined via a calibration curve which is instrument specifically generated by 2-point calibration and a master curve provided via the reagent barcode. The exact lot-specific calibrator values are encoded in the barcoded labels of the test-specific reagent.

The analyzer automatically calculates the analyte concentration of each sample in U/mL.

Example 3

Marker Discovery and Validation

In a first round of experiments, peptide array technology (JPT PepStar™) was employed to discover autoantibodies in patient sera. Peptide sequences from several 100's of proteins (potential targets of autoantibodies) were interrogated in the sample collective listed above.

The best differentiating candidates were then validated in the same sample cohort, but using different technology (Impact system, see below, and see Hornauer et al., Laborwelt 4 (2004), 38-39 and Hornauer et al., Biospectrum Special Proteomics 10 (2004), 564) and freshly synthesized/quality checked peptide sequences to enable sound technical validation.

The Impact technology is a system for multi-parameter measurement, where 10 different marker candidates can be investigated from one single sample aliquot. The markers to be tested are spotted on defined areas in the incubation chamber. In this case, the peptide sequences of interest were synthesized as biotinylated versions to be immobilized on streptavidin-coated spots on the Impact-chips.

Example 4

Identification of a Marker Panel for the Diagnosis of RA

Each autoantibody target was represented by a short sequence stretch as listed in table 2. The peptides contained biotin-PEG3 at the N-terminus for immobilization on the Impact chip, and terminated with an amide at the C-terminus to mimic the situation within the intact protein. For technical reasons, cysteines (C) were replaced by serines (S) as in SEQ ID NO:4.

TABLE 2

Marker sequences in validation

| Marker | Peptide sequence | Peptide name | Comments |
|---|---|---|---|
| anti-MCM3 | PATKKTIERRYSDLT | Y159 | SEQ ID NO: 1 |
| anti-Casp8 | NKSLLKIINDYEEFS | Y178 | SEQ ID NO: 2 |
| anti-PIK3CD | DQLKTGERCLYMWPS | Y440 | SEQ ID NO: 3 |
| anti-PIK3CD | DQLKTGERSLYMWPS | Y440* | SEQ ID NO: 4 |

3 novel marker candidates were validated with good results in discriminating RA from OA and other autoimmune diseases as shown in table 3.

As a reference the classification results for anti-CCP alone are presented, which is currently the only biochemical marker forming part of the ARA-criteria.

As shown in Tab. 3 the marker combination anti-CCP+ anti-PIK3CD and also the further displayed marker combinations allows to differentiate RA from OA and also to differentiate RA versus OA and other autoimmune diseases.

The aim of the current invention was to improve the correct diagnosis of RA versus controls including OA.

For the study population according to Example 1 and Table 1 a cut-off for the marker anti-[CCP] of 5 U/mL was selected.

For the study population according to Example 1 and Table 1 a cut-off for the marker anti-[Casp8] of 49.9 U/mL was selected.

For the study population according to Example 1 and Table 1 a cut-off for the marker anti-[MCM3] of 15.1 U/mL was selected.

For the study population according to Example 1 and Table 1 a cut-off for the marker anti-[PIK3CD] of 15.1 U/mL was selected.

TABLE 3

Diagnostic performance of new markers

| No of markers | Marker or marker panel | RA versus OA | | RA versus OA and other autoimmune diseases | |
|---|---|---|---|---|---|
| | | correct pos./ Sensitivity | correct neg./ Specificity | correct pos./ Sensitivity | correct neg./ Specificity |
| 1 | anti-CCP | 31.7% | 100% | 31.7% | 98.9% |
| 2 | anti-CCP, anti-MCM3 | 39.2% | 97.4% | 39.2% | 96.6% |
| 2 | anti-CCP, anti-Casp8 | 40.5% | 94.9% | 40.5% | 91.0% |

TABLE 3-continued

Diagnostic performance of new markers

| No of markers | Marker or marker panel | RA versus OA | | RA versus OA and other autoimmune diseases | |
|---|---|---|---|---|---|
| | | correct pos./ Sensitivity | correct neg./ Specificity | correct pos./ Sensitivity | correct neg./ Specificity |
| 2 | anti-CCP, anti-PIK3CD | 38.0% | 94.9% | 38.0% | 93.3% |
| 3 | anti-CCP, anti-MCM3, anti-Casp8 | 53.2% | 89.8% | 53.2% | 84.3% |
| 3 | anti-CCP, anti-MCM3, anti-PIK3CD | 51.9% | 89.7% | 51.9% | 86.5% |
| 3 | anti-CCP, anti-Casp8, anti-PIK3CD | 53.2% | 82.1% | 53.2% | 78.7% |
| 4 | anti-CCP, anti-MCM3, anti-Casp8, anti-PIK3CD | 63.3% | 82.1% | 63.3% | 74.2% |

The invention claimed is:

1. A method for assessing the absence or presence of rheumatoid arthritis (RA) in vitro by biochemical markers, comprising
   a) measuring in a whole blood, plasma or serum sample from a human subject the concentration of at least anti-cyclic citrullinated peptides (anti-CCP) and anti-PIK3CD;
   b) combining the concentration values measured for anti-CCP and anti-PIK3CD in (a); and
   c) correlating a combined value determined in step (b) with the absence or presence of RA, wherein an increased combined value compared to the cut-off combined concentration value measured for anti-CCP and anti-PIK3CD from a reference population is indicative for the presence of RA.

2. The method according to claim 1, wherein step (a) of the method is an immunoassay method.

3. The method according to claim 2, wherein anti-CCP and anti-PIK3CD are captured by one or more CCP as antigen and/or one or more PIK3CD as antigen, respectively.

4. The method according to claim 1, wherein the combined concentration values of step (b) are compared to a cut-off value derived from a reference population excluding RA-positive patients, comprising patients that have osteoarthritis (OA).

5. The method according to claim 1, further comprising the measurement of anti-MCM3.

6. A method for assessing a severity of rheumatoid arthritis (RA) in vitro by biochemical markers, comprising
   a) measuring in a whole blood, plasma or serum sample the concentration of at least anti-cyclic citrullinated peptides (anti-CCP) and anti-PIK3CD;
   b) combining the concentration values measured for anti-CCP and anti-PIK3CD in (a); and
   c) correlating from an combined value from (b) to the severity of RA, wherein the higher the combined value compared to the cut-off combined concentration value measured for anti-CCP and anti-PIK3CD from a reference population is indicative for the severity of RA in the patient.

7. A method for differentiation of rheumatoid arthritis (RA) from osteoarthritis (OA) in vitro by biochemical markers, comprising
   a) measuring in a whole blood, plasma or serum sample the concentration of at least anti-cyclic citrullinated peptides (anti-CCP) and anti-PIK3CD;
   b) combining the concentration values measured for anti-CCP and anti-PIK3CD in (a); and
   c) differentiating from an increased combined value from (b) RA from OA, wherein an increased combined value compared to the cut-off combined concentration value measured for anti-CCP and anti-PIK3CD from a reference population is indicative for the presence of RA.

8. A kit comprising: 1) peptide reagents comprising SEQ ID. No. 8 to specifically measure anti-CCP; and 2) peptide reagents comprising SEQ ID. No. 3, SEQ ID. No. 4 and/or SEQ ID. No. 7 to specifically measure anti-PIK3CD, and optionally auxiliary reagents for performing the measurement.

* * * * *

SEQUENCE LISTING

```
<160> NUMBER OF SEQ ID NOS: 8

<210> SEQ ID NO 1
<211> LENGTH: 15
<212> TYPE: PRT
<213> ORGANISM: Homo sapiens
<220> FEATURE:
<221> NAME/KEY: Y159
<222> LOCATION: (1)..(15)
<223> OTHER INFORMATION: anti-MCM3 peptide

<400> SEQUENCE: 1

Pro Ala Thr Lys Lys Thr Ile Glu Arg Arg Tyr Ser Asp Leu Thr
1               5                   10                  15

<210> SEQ ID NO 2
<211> LENGTH: 15
<212> TYPE: PRT
<213> ORGANISM: Homo sapiens
<220> FEATURE:
<221> NAME/KEY: Y178
<222> LOCATION: (1)..(15)
<223> OTHER INFORMATION: anti-Casp8 peptide

<400> SEQUENCE: 2

Asn Lys Ser Leu Leu Lys Ile Ile Asn Asp Tyr Glu Glu Phe Ser
1               5                   10                  15

<210> SEQ ID NO 3
<211> LENGTH: 15
<212> TYPE: PRT
<213> ORGANISM: Homo sapiens
<220> FEATURE:
<221> NAME/KEY: Y440
<222> LOCATION: (1)..(15)
<223> OTHER INFORMATION: anti-PIK3CD peptide

<400> SEQUENCE: 3

Asp Gln Leu Lys Thr Gly Glu Arg Cys Leu Tyr Met Trp Pro Ser
1               5                   10                  15

<210> SEQ ID NO 4
<211> LENGTH: 15
```

```
<212> TYPE: PRT
<213> ORGANISM: Homo sapiens
<220> FEATURE:
<221> NAME/KEY: Y440*
<222> LOCATION: (1)..(15)
<223> OTHER INFORMATION: anti-PIK3CD peptide

<400> SEQUENCE: 4

Asp Gln Leu Lys Thr Gly Glu Arg Ser Leu Tyr Met Trp Pro Ser
1               5                   10                  15

<210> SEQ ID NO 5
<211> LENGTH: 808
<212> TYPE: PRT
<213> ORGANISM: Homo sapiens
<220> FEATURE:
<221> NAME/KEY: misc_feature
<222> LOCATION: (1)..(808)
<223> OTHER INFORMATION: Minichromosome maintenance protein 3 (MCM3)
      human protein, SwissProt ID: P25205

<400> SEQUENCE: 5

Met Ala Gly Thr Val Val Leu Asp Asp Val Glu Leu Arg Glu Ala Gln
1               5                   10                  15

Arg Asp Tyr Leu Asp Phe Leu Asp Glu Glu Asp Gln Gly Ile Tyr
            20                  25                  30

Gln Ser Lys Val Arg Glu Leu Ile Ser Asp Asn Gln Tyr Arg Leu Ile
        35                  40                  45

Val Asn Val Asn Asp Leu Arg Arg Lys Asn Glu Lys Arg Ala Asn Arg
    50                  55                  60

Leu Leu Asn Asn Ala Phe Glu Glu Leu Val Ala Phe Gln Arg Ala Leu
65                  70                  75                  80

Lys Asp Phe Val Ala Ser Ile Asp Ala Thr Tyr Ala Lys Gln Tyr Glu
                85                  90                  95

Glu Phe Tyr Val Gly Leu Glu Gly Ser Phe Gly Ser Lys His Val Ser
            100                 105                 110

Pro Arg Thr Leu Thr Ser Cys Phe Leu Ser Cys Val Cys Val Glu
        115                 120                 125

Gly Ile Val Thr Lys Cys Ser Leu Val Arg Pro Lys Val Val Arg Ser
    130                 135                 140

Val His Tyr Cys Pro Ala Thr Lys Lys Thr Ile Glu Arg Arg Tyr Ser
145                 150                 155                 160

Asp Leu Thr Thr Leu Val Ala Phe Pro Ser Ser Val Tyr Pro Thr
                165                 170                 175

Lys Asp Glu Glu Asn Asn Pro Leu Glu Thr Glu Tyr Gly Leu Ser Val
            180                 185                 190

Tyr Lys Asp His Gln Thr Ile Thr Ile Gln Glu Met Pro Glu Lys Ala
        195                 200                 205

Pro Ala Gly Gln Leu Pro Arg Ser Val Asp Val Ile Leu Asp Asp
    210                 215                 220

Leu Val Asp Lys Ala Lys Pro Gly Asp Arg Val Gln Val Val Gly Thr
225                 230                 235                 240

Tyr Arg Cys Leu Pro Gly Lys Lys Gly Gly Tyr Thr Ser Gly Thr Phe
                245                 250                 255

Arg Thr Val Leu Ile Ala Cys Asn Val Lys Gln Met Ser Lys Asp Ala
            260                 265                 270

Gln Pro Ser Phe Ser Ala Glu Asp Ile Ala Lys Ile Lys Lys Phe Ser
        275                 280                 285
```

```
Lys Thr Arg Ser Lys Asp Ile Phe Asp Gln Leu Ala Lys Ser Leu Ala
290                 295                 300

Pro Ser Ile His Gly His Asp Tyr Val Lys Lys Ala Ile Leu Cys Leu
305                 310                 315                 320

Leu Leu Gly Gly Val Glu Arg Asp Leu Glu Asn Gly Ser His Ile Arg
                325                 330                 335

Gly Asp Ile Asn Ile Leu Leu Ile Gly Asp Pro Ser Val Ala Lys Ser
                340                 345                 350

Gln Leu Leu Arg Tyr Val Leu Cys Thr Ala Pro Arg Ala Ile Pro Thr
                355                 360                 365

Thr Gly Arg Gly Ser Ser Gly Val Gly Leu Thr Ala Ala Val Thr Thr
370                 375                 380

Asp Gln Glu Thr Gly Glu Arg Arg Leu Glu Ala Gly Ala Met Val Leu
385                 390                 395                 400

Ala Asp Arg Gly Val Val Cys Ile Asp Glu Phe Asp Lys Met Ser Asp
                405                 410                 415

Met Asp Arg Thr Ala Ile His Glu Val Met Glu Gln Gly Arg Val Thr
                420                 425                 430

Ile Ala Lys Ala Gly Ile His Ala Arg Leu Asn Ala Arg Cys Ser Val
                435                 440                 445

Leu Ala Ala Ala Asn Pro Val Tyr Gly Arg Tyr Asp Gln Tyr Lys Thr
450                 455                 460

Pro Met Glu Asn Ile Gly Leu Gln Asp Ser Leu Leu Ser Arg Phe Asp
465                 470                 475                 480

Leu Leu Phe Ile Met Leu Asp Gln Met Asp Pro Glu Gln Asp Arg Glu
                485                 490                 495

Ile Ser Asp His Val Leu Arg Met His Arg Tyr Arg Ala Pro Gly Glu
                500                 505                 510

Gln Asp Gly Asp Ala Met Pro Leu Gly Ser Ala Val Asp Ile Leu Ala
                515                 520                 525

Thr Asp Asp Pro Asn Phe Ser Gln Glu Asp Gln Asp Thr Gln Ile
530                 535                 540

Tyr Glu Lys His Asp Asn Leu Leu His Gly Thr Lys Lys Lys Glu
545                 550                 555                 560

Lys Met Val Ser Ala Ala Phe Met Lys Lys Tyr Ile His Val Ala Lys
                565                 570                 575

Ile Ile Lys Pro Val Leu Thr Gln Glu Ser Ala Thr Tyr Ile Ala Glu
                580                 585                 590

Glu Tyr Ser Arg Leu Arg Ser Gln Asp Ser Met Ser Ser Asp Thr Ala
                595                 600                 605

Arg Thr Ser Pro Val Thr Ala Arg Thr Leu Glu Thr Leu Ile Arg Leu
610                 615                 620

Ala Thr Ala His Ala Lys Ala Arg Met Ser Lys Thr Val Asp Leu Gln
625                 630                 635                 640

Asp Ala Glu Glu Ala Val Glu Leu Val Gln Tyr Ala Tyr Phe Lys Lys
                645                 650                 655

Val Leu Glu Lys Glu Lys Arg Lys Arg Ser Glu Asp Glu Ser
                660                 665                 670

Glu Thr Glu Asp Glu Glu Glu Lys Ser Gln Glu Asp Gln Glu Gln Lys
                675                 680                 685

Arg Lys Arg Arg Lys Thr Arg Gln Pro Asp Ala Lys Asp Gly Asp Ser
690                 695                 700

Tyr Asp Pro Tyr Asp Phe Ser Asp Thr Glu Glu Glu Met Pro Gln Val
```

```
                  705                 710                 715                 720
His Thr Pro Lys Thr Ala Asp Ser Gln Glu Thr Lys Glu Ser Gln Lys
                    725                 730                 735

Val Glu Leu Ser Glu Ser Arg Leu Lys Ala Phe Lys Val Ala Leu Leu
                740                 745                 750

Asp Val Phe Arg Glu Ala His Ala Gln Ser Ile Gly Met Asn Arg Leu
                755                 760                 765

Thr Glu Ser Ile Asn Arg Asp Ser Glu Pro Phe Ser Ser Val Glu
                770                 775                 780

Ile Gln Ala Ala Leu Ser Lys Met Gln Asp Asp Asn Gln Val Met Val
785                 790                 795                 800

Ser Glu Gly Ile Ile Phe Leu Ile
                805

<210> SEQ ID NO 6
<211> LENGTH: 479
<212> TYPE: PRT
<213> ORGANISM: Homo sapiens
<220> FEATURE:
<221> NAME/KEY: misc_feature
<222> LOCATION: (1)..(479)
<223> OTHER INFORMATION: Caspase-8 (Casp8) human protein, SwissProt ID:
      Q14790

<400> SEQUENCE: 6

Met Asp Phe Ser Arg Asn Leu Tyr Asp Ile Gly Glu Gln Leu Asp Ser
1               5                   10                  15

Glu Asp Leu Ala Ser Leu Lys Phe Leu Ser Leu Asp Tyr Ile Pro Gln
                20                  25                  30

Arg Lys Gln Glu Pro Ile Lys Asp Ala Leu Met Leu Phe Gln Arg Leu
            35                  40                  45

Gln Glu Lys Arg Met Leu Glu Glu Ser Asn Leu Ser Phe Leu Lys Glu
        50                  55                  60

Leu Leu Phe Arg Ile Asn Arg Leu Asp Leu Leu Ile Thr Tyr Leu Asn
65                  70                  75                  80

Thr Arg Lys Glu Glu Met Glu Arg Glu Leu Gln Thr Pro Gly Arg Ala
                85                  90                  95

Gln Ile Ser Ala Tyr Arg Val Met Leu Tyr Gln Ile Ser Glu Glu Val
            100                 105                 110

Ser Arg Ser Glu Leu Arg Ser Phe Lys Phe Leu Leu Gln Glu Glu Ile
        115                 120                 125

Ser Lys Cys Lys Leu Asp Asp Asp Met Asn Leu Leu Asp Ile Phe Ile
    130                 135                 140

Glu Met Glu Lys Arg Val Ile Leu Gly Glu Gly Lys Leu Asp Ile Leu
145                 150                 155                 160

Lys Arg Val Cys Ala Gln Ile Asn Lys Ser Leu Leu Lys Ile Ile Asn
                165                 170                 175

Asp Tyr Glu Glu Phe Ser Lys Glu Arg Ser Ser Ser Leu Glu Gly Ser
            180                 185                 190

Pro Asp Glu Phe Ser Asn Gly Glu Glu Leu Cys Gly Val Met Thr Ile
        195                 200                 205

Ser Asp Ser Pro Arg Glu Gln Asp Ser Glu Ser Gln Thr Leu Asp Lys
    210                 215                 220

Val Tyr Gln Met Lys Ser Lys Pro Arg Gly Tyr Cys Leu Ile Ile Asn
225                 230                 235                 240

Asn His Asn Phe Ala Lys Ala Arg Glu Lys Val Pro Lys Leu His Ser
```

245                 250                 255
Ile Arg Asp Arg Asn Gly Thr His Leu Asp Ala Gly Ala Leu Thr Thr
            260                 265                 270

Thr Phe Glu Glu Leu His Phe Glu Ile Lys Pro His Asp Asp Cys Thr
        275                 280                 285

Val Glu Gln Ile Tyr Glu Ile Leu Lys Ile Tyr Gln Leu Met Asp His
    290                 295                 300

Ser Asn Met Asp Cys Phe Ile Cys Cys Ile Leu Ser His Gly Asp Lys
305                 310                 315                 320

Gly Ile Ile Tyr Gly Thr Asp Gly Gln Glu Ala Pro Ile Tyr Glu Leu
                325                 330                 335

Thr Ser Gln Phe Thr Gly Leu Lys Cys Pro Ser Leu Ala Gly Lys Pro
            340                 345                 350

Lys Val Phe Phe Ile Gln Ala Cys Gln Gly Asp Asn Tyr Gln Lys Gly
        355                 360                 365

Ile Pro Val Glu Thr Asp Ser Glu Glu Gln Pro Tyr Leu Glu Met Asp
    370                 375                 380

Leu Ser Ser Pro Gln Thr Arg Tyr Ile Pro Asp Glu Ala Asp Phe Leu
385                 390                 395                 400

Leu Gly Met Ala Thr Val Asn Asn Cys Val Ser Tyr Arg Asn Pro Ala
                405                 410                 415

Glu Gly Thr Trp Tyr Ile Gln Ser Leu Cys Gln Ser Leu Arg Glu Arg
            420                 425                 430

Cys Pro Arg Gly Asp Asp Ile Leu Thr Ile Leu Thr Glu Val Asn Tyr
        435                 440                 445

Glu Val Ser Asn Lys Asp Asp Lys Lys Asn Met Gly Lys Gln Met Pro
    450                 455                 460

Gln Pro Thr Phe Thr Leu Arg Lys Lys Leu Val Phe Pro Ser Asp
465                 470                 475

<210> SEQ ID NO 7
<211> LENGTH: 1044
<212> TYPE: PRT
<213> ORGANISM: Homo sapiens
<220> FEATURE:
<221> NAME/KEY: misc_feature
<222> LOCATION: (1)..(1044)
<223> OTHER INFORMATION: Phosphatidylinositol-4,5-bisphosphate 3-kinase
      catalytic subunit PI3-Kinase (PIK3CD) human protein, SwissProt
      ID: O00329

<400> SEQUENCE: 7

Met Pro Pro Gly Val Asp Cys Pro Met Glu Phe Trp Thr Lys Glu Glu
1               5                   10                  15

Asn Gln Ser Val Val Val Asp Phe Leu Leu Pro Thr Gly Val Tyr Leu
            20                  25                  30

Asn Phe Pro Val Ser Arg Asn Ala Asn Leu Ser Thr Ile Lys Gln Leu
        35                  40                  45

Leu Trp His Arg Ala Gln Tyr Glu Pro Leu Phe His Met Leu Ser Gly
    50                  55                  60

Pro Glu Ala Tyr Val Phe Thr Cys Ile Asn Gln Thr Ala Glu Gln Gln
65                  70                  75                  80

Glu Leu Glu Asp Glu Gln Arg Arg Leu Cys Asp Val Gln Pro Phe Leu
                85                  90                  95

Pro Val Leu Arg Leu Val Ala Arg Glu Gly Asp Arg Val Lys Lys Leu
            100                 105                 110

-continued

Ile Asn Ser Gln Ile Ser Leu Leu Ile Gly Lys Gly Leu His Glu Phe
115                 120                 125

Asp Ser Leu Cys Asp Pro Glu Val Asn Asp Phe Arg Ala Lys Met Cys
130                 135                 140

Gln Phe Cys Glu Glu Ala Ala Ala Arg Arg Gln Gln Leu Gly Trp Glu
145                 150                 155                 160

Ala Trp Leu Gln Tyr Ser Phe Pro Leu Gln Leu Glu Pro Ser Ala Gln
                165                 170                 175

Thr Trp Gly Pro Gly Thr Leu Arg Leu Pro Asn Arg Ala Leu Leu Val
                180                 185                 190

Asn Val Lys Phe Glu Gly Ser Glu Glu Ser Phe Thr Phe Gln Val Ser
                195                 200                 205

Thr Lys Asp Val Pro Leu Ala Leu Met Ala Cys Ala Leu Arg Lys Lys
210                 215                 220

Ala Thr Val Phe Arg Gln Pro Leu Val Glu Gln Pro Glu Asp Tyr Thr
225                 230                 235                 240

Leu Gln Val Asn Gly Arg His Glu Tyr Leu Tyr Gly Ser Tyr Pro Leu
                245                 250                 255

Cys Gln Phe Gln Tyr Ile Cys Ser Cys Leu His Ser Gly Leu Thr Pro
                260                 265                 270

His Leu Thr Met Val His Ser Ser Ile Leu Ala Met Arg Asp Glu
275                 280                 285

Gln Ser Asn Pro Ala Pro Gln Val Gln Lys Pro Arg Ala Lys Pro Pro
290                 295                 300

Pro Ile Pro Ala Lys Lys Pro Ser Ser Val Ser Leu Trp Ser Leu Glu
305                 310                 315                 320

Gln Pro Phe Arg Ile Glu Leu Ile Gln Gly Ser Lys Val Asn Ala Asp
                325                 330                 335

Glu Arg Met Lys Leu Val Val Gln Ala Gly Leu Phe His Gly Asn Glu
                340                 345                 350

Met Leu Cys Lys Thr Val Ser Ser Ser Glu Val Ser Val Cys Ser Glu
                355                 360                 365

Pro Val Trp Lys Gln Arg Leu Glu Phe Asp Ile Asn Ile Cys Asp Leu
370                 375                 380

Pro Arg Met Ala Arg Leu Cys Phe Ala Leu Tyr Ala Val Ile Glu Lys
385                 390                 395                 400

Ala Lys Lys Ala Arg Ser Thr Lys Lys Lys Ser Lys Lys Ala Asp Cys
                405                 410                 415

Pro Ile Ala Trp Ala Asn Leu Met Leu Phe Asp Tyr Lys Asp Gln Leu
                420                 425                 430

Lys Thr Gly Glu Arg Cys Leu Tyr Met Trp Pro Ser Val Pro Asp Glu
                435                 440                 445

Lys Gly Glu Leu Leu Asn Pro Thr Gly Thr Val Arg Ser Asn Pro Asn
                450                 455                 460

Thr Asp Ser Ala Ala Leu Leu Ile Cys Leu Pro Glu Val Ala Pro
465                 470                 475                 480

His Pro Val Tyr Tyr Pro Ala Leu Glu Lys Ile Leu Glu Leu Gly Arg
                485                 490                 495

His Ser Glu Cys Val His Val Thr Glu Glu Gln Leu Gln Leu Arg
                500                 505                 510

Glu Ile Leu Glu Arg Arg Gly Ser Gly Glu Leu Tyr Glu His Glu Lys
                515                 520                 525

Asp Leu Val Trp Lys Leu Arg His Glu Val Gln Glu His Phe Pro Glu

```
            530                 535                 540
Ala Leu Ala Arg Leu Leu Leu Val Thr Lys Trp Asn Lys His Glu Asp
545                 550                 555                 560

Val Ala Gln Met Leu Tyr Leu Leu Cys Ser Trp Pro Glu Leu Pro Val
                565                 570                 575

Leu Ser Ala Leu Glu Leu Leu Asp Phe Ser Phe Pro Asp Cys His Val
                580                 585                 590

Gly Ser Phe Ala Ile Lys Ser Leu Arg Lys Leu Thr Asp Asp Glu Leu
                595                 600                 605

Phe Gln Tyr Leu Leu Gln Leu Val Gln Val Leu Lys Tyr Glu Ser Tyr
                610                 615                 620

Leu Asp Cys Glu Leu Thr Lys Phe Leu Leu Asp Arg Ala Leu Ala Asn
625                 630                 635                 640

Arg Lys Ile Gly His Phe Leu Phe Trp His Leu Arg Ser Glu Met His
                645                 650                 655

Val Pro Ser Val Ala Leu Arg Phe Gly Leu Ile Leu Glu Ala Tyr Cys
                660                 665                 670

Arg Gly Ser Thr His His Met Lys Val Leu Met Lys Gln Gly Glu Ala
                675                 680                 685

Leu Ser Lys Leu Lys Ala Leu Asn Asp Phe Val Lys Leu Ser Ser Gln
690                 695                 700

Lys Thr Pro Lys Pro Gln Thr Lys Glu Leu Met His Leu Cys Met Arg
705                 710                 715                 720

Gln Glu Ala Tyr Leu Glu Ala Leu Ser His Leu Gln Ser Pro Leu Asp
                725                 730                 735

Pro Ser Thr Leu Leu Ala Glu Val Cys Val Glu Gln Cys Thr Phe Met
                740                 745                 750

Asp Ser Lys Met Lys Pro Leu Trp Ile Met Tyr Ser Asn Glu Glu Ala
                755                 760                 765

Gly Ser Gly Gly Ser Val Gly Ile Ile Phe Lys Asn Gly Asp Asp Leu
                770                 775                 780

Arg Gln Asp Met Leu Thr Leu Gln Met Ile Gln Leu Met Asp Val Leu
785                 790                 795                 800

Trp Lys Gln Glu Gly Leu Asp Leu Arg Met Thr Pro Tyr Gly Cys Leu
                805                 810                 815

Pro Thr Gly Asp Arg Thr Gly Leu Ile Glu Val Val Leu Arg Ser Asp
                820                 825                 830

Thr Ile Ala Asn Ile Gln Leu Asn Lys Ser Asn Met Ala Ala Thr Ala
                835                 840                 845

Ala Phe Asn Lys Asp Ala Leu Leu Asn Trp Leu Lys Ser Lys Asn Pro
850                 855                 860

Gly Glu Ala Leu Asp Arg Ala Ile Glu Glu Phe Thr Leu Ser Cys Ala
865                 870                 875                 880

Gly Tyr Cys Val Ala Thr Tyr Val Leu Gly Ile Gly Asp Arg His Ser
                885                 890                 895

Asp Asn Ile Met Ile Arg Glu Ser Gly Gln Leu Phe His Ile Asp Phe
                900                 905                 910

Gly His Phe Leu Gly Asn Phe Lys Thr Lys Phe Gly Ile Asn Arg Glu
                915                 920                 925

Arg Val Pro Phe Ile Leu Thr Tyr Asp Phe Val His Val Ile Gln Gln
                930                 935                 940

Gly Lys Thr Asn Asn Ser Glu Lys Phe Glu Arg Phe Arg Gly Tyr Cys
945                 950                 955                 960
```

```
Glu Arg Ala Tyr Thr Ile Leu Arg Arg His Gly Leu Leu Phe Leu His
                965             970             975

Leu Phe Ala Leu Met Arg Ala Ala Gly Leu Pro Glu Leu Ser Cys Ser
            980             985             990

Lys Asp Ile Gln Tyr Leu Lys Asp  Ser Leu Ala Leu Gly  Lys Thr Glu
        995             1000             1005

Glu Glu  Ala Leu Lys His Phe  Arg Val Lys Phe Asn  Glu Ala Leu
    1010             1015             1020

Arg Glu  Ser Trp Lys Thr Lys  Val Asn Trp Leu Ala  His Asn Val
    1025             1030             1035

Ser Lys  Asp Asn Arg Gln
    1040

<210> SEQ ID NO 8
<211> LENGTH: 21
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: Cysteine for disulfide bond
<220> FEATURE:
<221> NAME/KEY: MISC_FEATURE
<222> LOCATION: (9)..(9)
<223> OTHER INFORMATION: X stands for citrulline
<220> FEATURE:
<221> NAME/KEY: MISC_FEATURE
<222> LOCATION: (16)..(16)
<223> OTHER INFORMATION: Cysteine for disulfide bond

<400> SEQUENCE: 8

His Gln Cys His Gln Glu Ser Thr Xaa Gly Arg Ser Arg Gly Arg Cys
1               5                   10                  15

Gly Arg Ser Gly Ser
            20
```